United States Patent [19]

Kawabuchi et al.

[11] 4,224,829
[45] Sep. 30, 1980

[54] TWO-DIMENSIONAL LINEAR B-SCAN ULTRASOUND DIAGNOSTIC APPARATUS WITH PHASE AND AMPLITUDE TAPERING

[75] Inventors: Masami Kawabuchi; Jun-ichi Sato; Kiyotaka Nagai; Hiroshi Fukukita; Akira Fukumoto, all of Kawasaki, Japan

[73] Assignee: Matsushita Electric Industrial Co., Ltd., Osaka, Japan

[21] Appl. No.: 962,609

[22] Filed: Nov. 21, 1978

[30] Foreign Application Priority Data

May 30, 1978 [JP] Japan ................................. 53/65206

[51] Int. Cl.³ .......................................... G01N 29/00
[52] U.S. Cl. .................................................. 73/626
[58] Field of Search ........................ 73/626, 625, 628; 128/660; 340/1 R, 3 R; 310/336; 367/103, 105

[56] References Cited

U.S. PATENT DOCUMENTS

| | | | |
|---|---|---|---|
| 3,881,466 | 5/1975 | Wilcox | 73/626 |
| 3,911,730 | 10/1975 | Niklas | 73/626 |
| 4,101,795 | 7/1978 | Fukumoto et al. | 310/336 |
| 4,140,107 | 2/1979 | Lancée et al. | 73/626 |
| 4,149,420 | 4/1979 | Hutchison et al. | 73/626 |

FOREIGN PATENT DOCUMENTS

2643918  3/1978  Fed. Rep. of Germany .............. 73/626

*Primary Examiner*—Stephen A. Kreitman
*Attorney, Agent, or Firm*—Lowe, King, Price & Becker

[57] ABSTRACT

An ultrasound diagnostic apparatus includes a linear array of piezoelectric transducers or plates with a width-to-thickness ratio of less than 0.8 and a control circuit which includes a transmitter and a receiver. The transmitter comprises a plurality of transmitting channels each including a local oscillator for generating an ultrasonic pulse in response to a clock signal. The plurality of such ultrasonic pulses are applied through a switching network to a selected group of successively arranged piezoelectric transducers to transmit a beam of ultrasonic energy into a human body. Each of the ultrasonic pulses is phase shifted and amplitude modulated with respect to the ultrasonic pulses of the other transmitting channels to provide phase and amplitude taper which results in a narrow width beam through the depth of the body. The ultrasonic energy returned from discontinuities between different tissues is detected by the activated transducers and applied through the switching network to the receiver in which each of the return signals is phase shifted and amplitude modulated with respect to the other signals to provide an output signal which is displayed on a cathode ray tube screen.

9 Claims, 7 Drawing Figures

TWO-DIMENSIONAL LINEAR B-SCAN ULTRASOUND DIAGNOSTIC APPARATUS WITH PHASE AND AMPLITUDE TAPERING

BACKGROUND OF THE INVENTION

1. Field of the Invention

The present invention relates to an ultrasound diagnostic apparatus of the B-scan type which forms pictorial images of two-dimensional cross sections through a biological body on a cathode ray tube to yield information about the internal structure of the body.

2. Description of the Prior Art

In recent years much effort has been spent on improving ultrasound techniques used in medical diagnosis. While the one-dimensional A-scan technique has proved to be very useful as a diagnostic tool for several parts of the body, the two-dimensional B-scan method has shown advantages over the A-scan method in several respects. One prior art B-scan method involves the use of a sector scanner discussed by J. C. Sommer in Ultrasonics, July 1962, pages 153-159, in which the beam transmitted from a linear array of electromechanical transducers is deflected through an angle by means of an electrically variable delay circuit which introduces a variable delay time as a function of time. This sector scan permits transmission of ultrasonic energy through the narrow spaces between the bone structures of adjacent ribs into the heart of the body to investigate its vertical cross sections.

Another B-scan method involves the use of a linear scanner as disclosed in U.S. Pat. No. 3,881,466 titled "Ultrasonic Cross-sectional Imaging System", in which the ultrasonic beam transmitted from a selected group of transducers, is shifted linearly through a linear array of such transducers. However, the prior art scanners have proved to be unsatisfactory in terms of resolution and signal-to-noise ratio.

U.S. Pat. No. 4,101,795, granted to Fukumoto et al and assigned to the same assignee as the present invention, discloses a piezoelectric transducer composed of a ceramic planar body with a width-to-thickness ratio equal to or smaller than 0.8 having an electromechanical coupling coefficient close to $k_{33}$ or $k'_{33}$. This transducer provides a vibration mode which is free from unwanted vibrations within the active frequency bandwidth due to the small width as compared to prior art transducers.

SUMMARY OF THE INVENTION

An object of the invention is to provide a compact, easy-to-handle linear B-scan diagnostic apparatus which provides clear pictorial images of two-dimensional cross sections of a living organ.

The invention contemplates the use of a linear array of piezoelectric transducers of the above-mentioned U.S. Patent in combination with an electronic drive circuit which enables a selected group of transducers to transmit ultrasonic pulses to form an ultrasonic beam and shifts the position of the beam in response to a clock pulse through the array of the transducers. The driving circuit includes phase and amplitude tapering circuit which causes the ultrasonic pulses to be spaced at delay intervals within the clock interval and amplitude modulated such that the transmitted ultrasonic waves are tapered in phase and amplitude so that the beam is formed into a narrow beam throughout the full depth of the subject body.

BRIEF DESCRIPTION OF THE DRAWINGS

The invention will be further described by way of example with reference to the accompanying drawings, in which.

DETAILED DESCRIPTION

Figure 1:
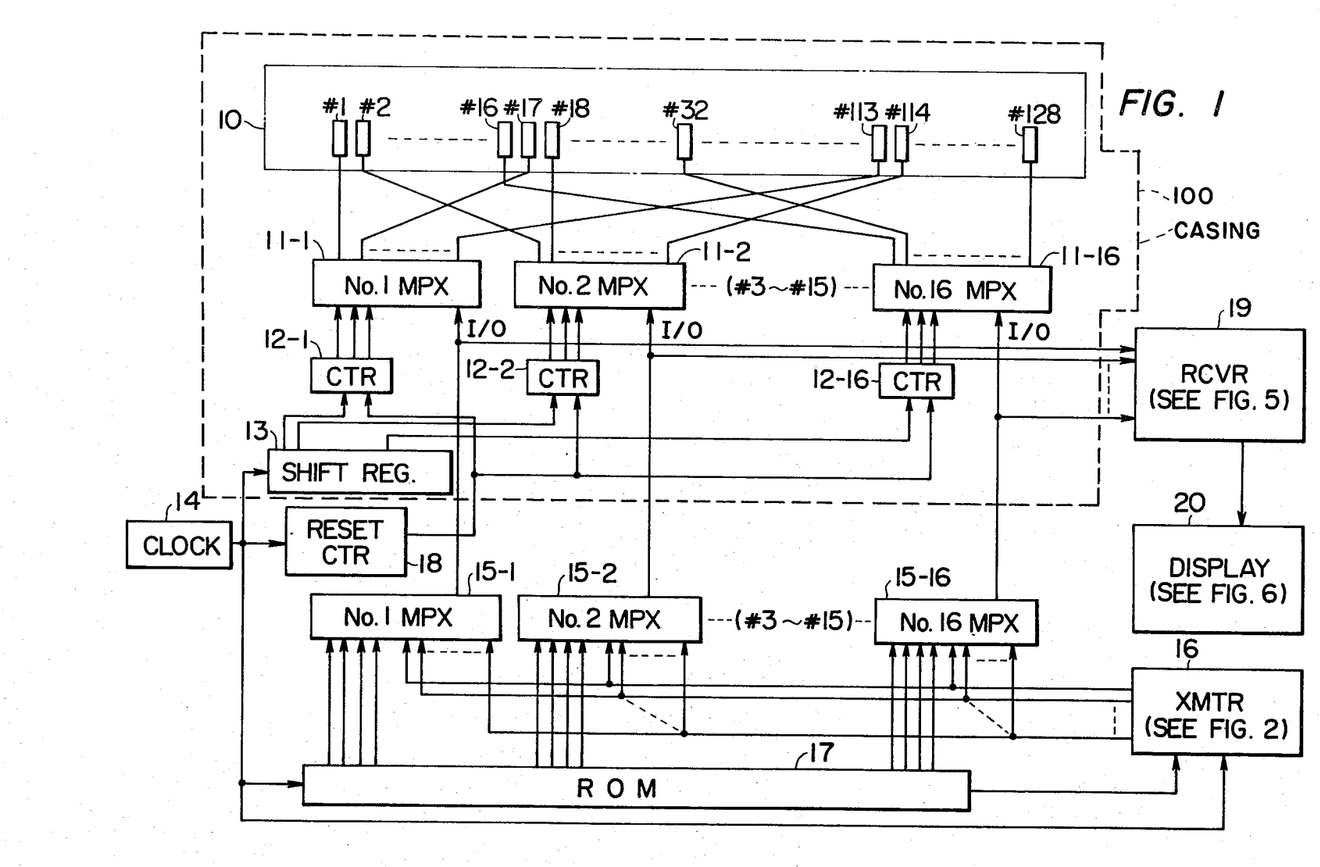
FIG. 1 is a schematic block diagram of the ultrasonic diagnostic apparatus of the invention.

The ultrasound diagnostic system of the invention depicted in FIG. 1 comprises a transducer unit 10 having an array of 128 piezoelectric ultrasound elements for transmission of ultrasonic sound pulses and reception of returned echo signals. There is provided a plurality of analog multiplexers or switching means 11-1 through 11-16 each having eight output terminals which are connected to the individual transducer elements such that No. 1 output terminals of the multiplexers 11-1 to 11-16 are connected to No. 1 to No. 16 transducer elements respectively, No. 2 output terminals being respectively connected to No. 17 to No. 32 elements and so on, so that No. 8 terminals are connected to No. 113 to No. 128 elements, respectively. Counters 12-1 to 12-16 are provided which are activated one after another in response to an output signal from a 16-bit shift register 13 generated in response to a clock pulse received from clock source 14 at a repetition frequency of 3 to 4 kHz depending on the depth of a body to be investigated. The output signal of the shift register is shifted from the leftmost to the rightmost bit positions in response to the clock pulse until the rightmost 16th bit position is reached whereupon the above process is repeated until all the counters 12 are cleared by a reset signal generated by a reset counter 18 when it receives a 128th clock pulse. After the resetting operation, the process is repeated again. Responsive to each input signal from the shift register, each counter provides an output which is a three-bit binary representation of the number of pulses it has received. The three-bit binary representation indicates a corresponding address or selected one of 8 output terminals of the associated multiplexer. Each multiplexer thus establishes a signal access path from an input/output terminal I/O to the selected output terminal to activate the associated transducer element and this access path is maintained until the next clock pulse. The output terminals of each multiplexer is activated in succession from the leftmost bit position to the rightmost bit position, so that in response to a sixteenth clock pulse transducers No. 1 through No. 16 are simultaneously activated and in response to the occurrence of the seventeenth clock pulse counter 12-1 changes its binary output while the other counters remain unchanged so that transducers No. 2 to No. 17 will be simultaneously activated. This process is repeated until the occurrence of the 128th clock pulse whereupon transducers No. 113 to No. 128 are simultaneously activated. It is therefore appreciated that in response to each clock pulse one of the multiplexers 11-1 to 11-16 is caused to change its access path to the next, so that a group of successively arranged sixteen transducers are activated simultaneously during the interval between successive clock pulses, and the activated group is shifted to the right by the width of one transducer.

A second group of analog multiplexers or switching means 15-1 to 15-16 is provided. Each of these multiplexers has a single output terminal which is connected to the input/output terminal I/O of the multiplexers 11-1 to 11-16, respectively, and a set of sixteen signal input terminals which are connected in multiple to the signal input terminals of the other multiplexers and thence to the output terminals of a transmitter 16. These multiplexers are individually in receipt of a four-bit address code from a read-only memory 17 in order to establish connections between the output terminals of the transmitter 16 and the activated ones of the transducers. As will be explained below, the transmitter 16 generates a set of ultrasonic pulses which are so amplitude modulated and phase shifted as to give amplitude and phase tapers to the main beam so that the radiated beam width is narrowed with a focus point at a selected depth from the entry surface. The memory unit 17 is so programmed that it permits the activated transducers to transmit ultrasound pulses of the same directional pattern for each group of activated transducers.

Responsive to each clock pulse from source 14 there is produced a set of 16 ultrasound pulses which are transmitted into a subject body and within the interval between successive clock pulses the return signal is received by the activated transducers and applied to a receiver unit 19. As will be described, the received signals are phase-shifted and amplitude-modulated in accordance with a preset pattern and applied to a display unit 20.

Figure 2:
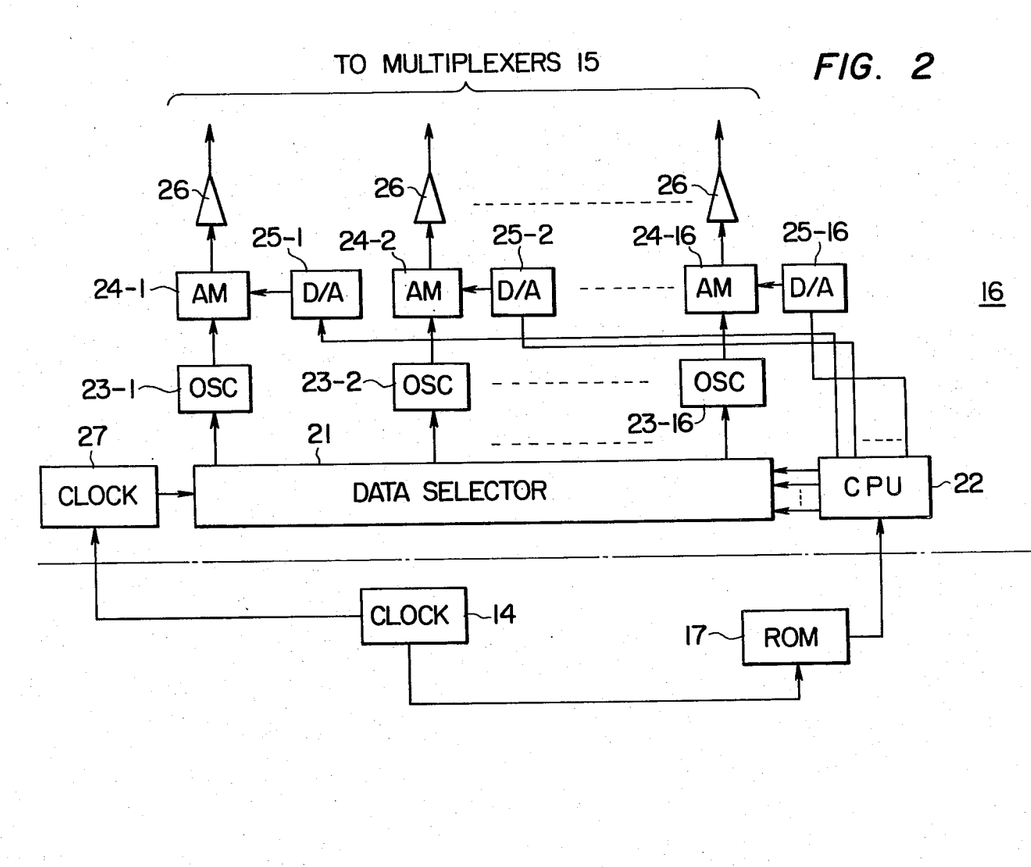
FIG. 2 is an illustration of the detail of the transmitter unit of FIG. 1.

Referring to FIG. 2 details of the transmitter 16 are illustrated as comprising a data selector 21 which receives from the clock comprising a clock source 27 which receives clock pulses from the first clock source 14 to generate a train of higher rate clock pulses at 20-nanosecond intervals in response to each clock pulse from source 14 and supplies the higher rate of clock pulses to a data selector or timing control circuit 21. This data selector is also in receipt of timing control signals from a central processor unit 22 of a general-purpose computer. The data selector 21 provides an enabling signal to each one of a plurality of pulsed-oscillator 23-1 to 23-16 at intervals dictated by the control signals from the processor unit 22. This timing control is accomplished by programming the memory unit 17 in such manner that the data selector 21 generates an output at a predetermined number of higher rate clock pulses. Therefore, the time intervals between successive enabling pulses are an integral multiple of 20-nanosecond duration. The delay time of each activated transducer Ti is determined by the following formula where the suffix "i" is an integer ranging from unity to 16 representing the position of the transducer with respect to a reference position:

$$Ti = \frac{1}{C} \left\{ \sqrt{F^2 + (\frac{n-1}{2})^2 d^2} - \sqrt{F^2 + (\frac{n+1}{2} - i)^2 d^2} \right\} \quad (1)$$

where,
C: velocity of sound within human body,
n: number of simultaneously activated transducers to provide a main beam (in this embodiment, 16),
F: focal distance of the main beam, and
d: center-to-center spacing between transducers.

Figure 3:
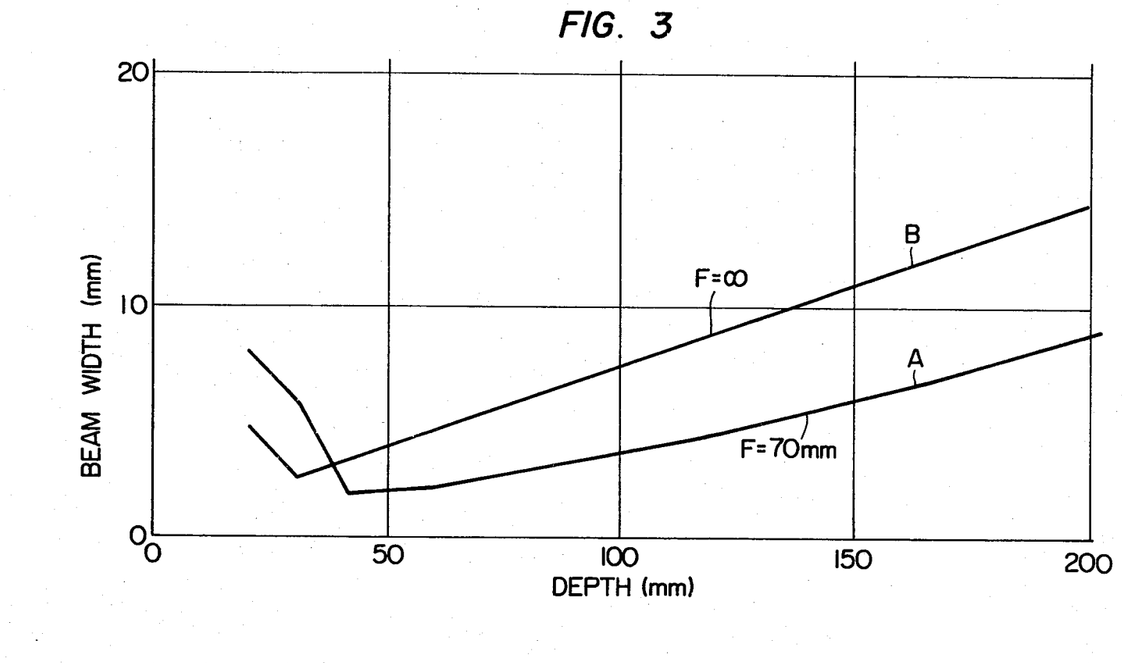
FIG. 3 is a graphic illustration of the effect of phase tapering on the beam width.

The oscillators 23 are activated in response to the enabling pulses from the data selector 21 to generate a set of 16 bursts of ultrasonic frequency, the burst signals being applied respectively to amplitude modulators 24-1 to 24-16 to be amplitude modulated in accordance with voltage outputs from digital-analog converters 25-1 to 25-16 which are coupled to receive data representing weighting factors stored in memory 17 to provide amplitude taper to the main transmit beam. The amplitude modulated signals are coupled through buffer amplifiers 26 to the input terminals of the multiplexers 15. This amplitude and phase tapering results in a beam width as graphically illustrated in FIG. 3 as a function of depth from the surface of the subject human body. Curve A represents the characteristic of the device having a focal distance F of 70 millimeters and curve B representing the characteristic with an infinite focal distance. As will be seen from FIG. 3, the beam tends to have a greater width in a range of depths less than 40 millimeters than it has at greater depths. This beam width widening at the shallow region will be compensated for by the amplitude and phase tapering in the receiver unit 19.

Figure 4:
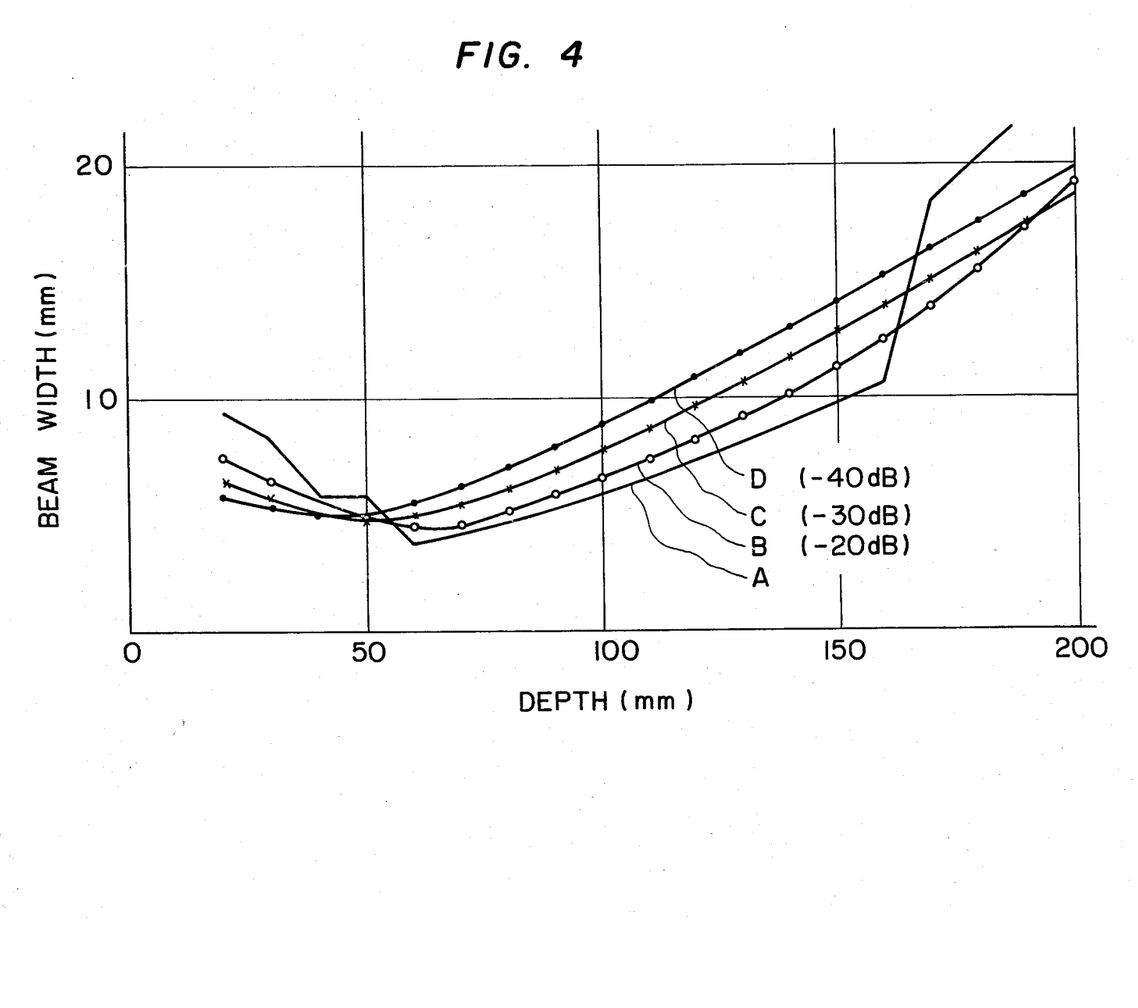
FIG. 4 is a graphic illustration of the effect of amplitude tapering on the beam width.

A variety of methods are considered for providing a distribution of weighting factors. For example, the weighting factors are distributed based on the Tchebysheff polynomial. FIG. 4 illustrates the effect of the Tchebysheff polynomial distribution on the beam width of phase-tapered beam as a function of depth from the entry surface with the vertical axis representing the beam width at −20 dB points and the horizontal axis representing the depth. Curve A represents the characteristic of a phase-tapered beam having no amplitude taper, while curves B, C, D represent those of phase-and-amplitude tapered beams with different sidelobe levels. As shown curves B, C and D are compared favorably with curve A with respect to the shallow and deep regions.

Figure 5:
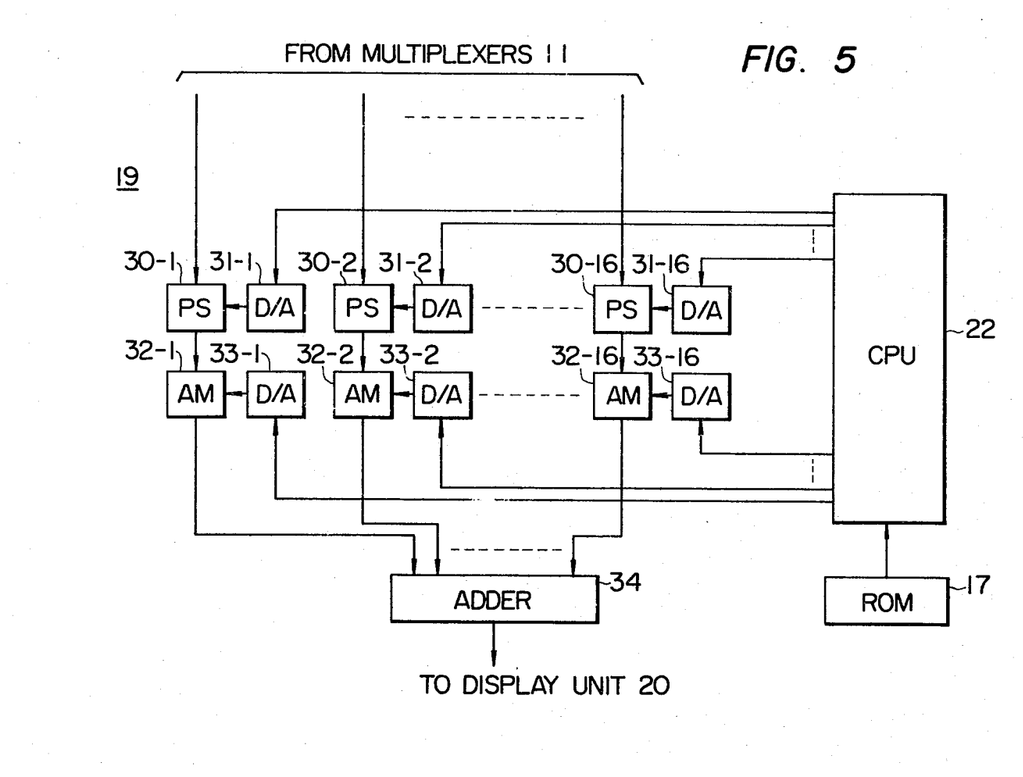
FIG. 5 is an illustration of the detail of the receiver unit of FIG. 1.

Referring to FIG. 5 the receiver unit 19 is shown in detail. Within the interval between successive clock pulses of source 14, the transmitted ultrasonic energy is reflected from discontinuities present in the patient body and detected by the transducers to convert the returned energy into electrical signals which are coupled to the receiver 19 via the multiplexers 11. The returned signals are applied to a plurality of phase shifters 30-1 through 30-16 in which they undergo phase shifters accordance with Equation 1 described previously. This is achieved by a plurality of digital-analog converters 31-1 through 31-16 coupled to the central processor unit 22 in an identical manner to that described with reference to FIG. 2. In this case, however, the focal distance F is so chosen as to decrease the beam width at depths smaller than about 40 mm. The phase-shifted signals are then applied to amplitude modulators 32-1 to 32-16 in which the signals are amplitude modulated in accordance with the instructions from the central processor unit 22 via digital-analog converters 33-1 to 33-16 in such manner that the equivalent receiving aperture of the transducer unit 10 is varied as a function of time to provide a reduced sidelobe level, so that the power of resolution in the lateral direction is improved. The phase-and-amplitude modulated signals are applied to an adder 34 and thence to the display unit 20.

Figures 6, 7:
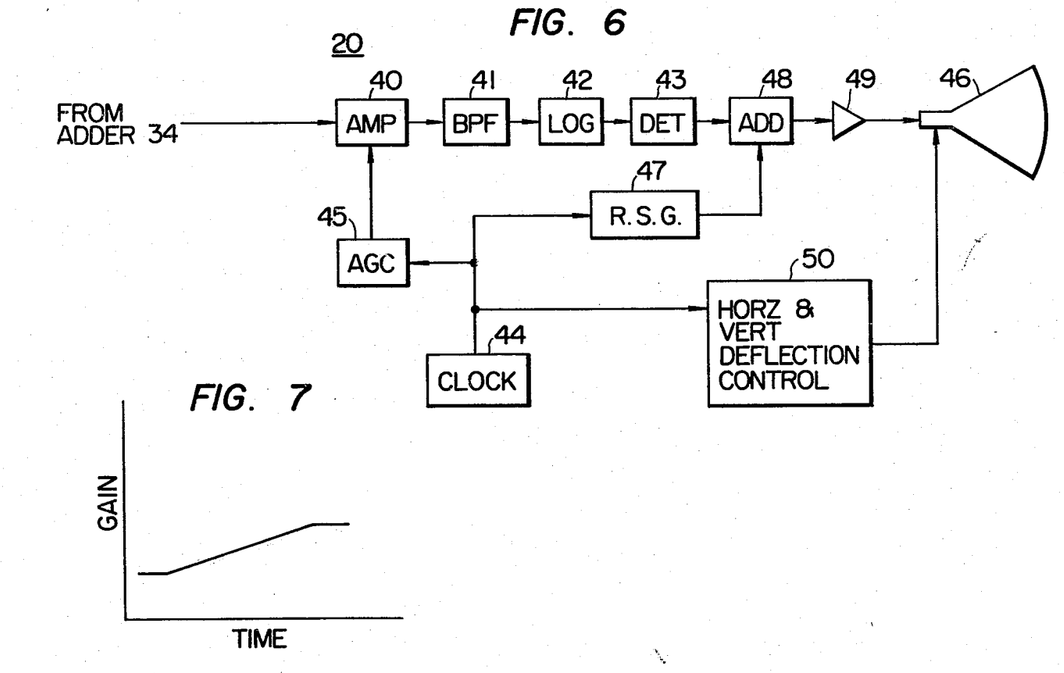
FIG. 6 is an illustration of the detail of the display unit of FIG. 1.
FIG. 7 shows the operating characteristic of an automatic gain control circuit of FIG. 6.

As illustrated in FIG. 6, the output signal from the receiver unit 19 is coupled to an automatic gain controlled amplifier 40, thence to a bandpass filter 41 and through a logarithmic amplifier 42 to a detector 43. A source of clock pulses 44 is provided to supply clock pulses to a gain control circuit 45 which generates a voltage signal variable as a function of time in response to a clock pulse supplied from the clock source 44, as shown in FIG. 7. The reason for this is to compensate for the exponentially increasing attenuation of the transmitted ultrasound as a function of depth. In a practical embodiment where ultrasound frequency is 2.5 MHz, the gain-controlled amplifier 40 is designed to have a control range of 60 dB so as to compensate for the loss encountered at a depth of 200 millimeters, since in the human body the 1 MHz ultrasound undergoes a loss of 1 dB as it travels a distance of 10 millimeters. The bandpass filter 41 is tuned to the frequency of the ultrasound to reject noise. The log amplifier 42 acts as a signal compressor to reduce the dynamic range of the signal to conform to the dynamic range of the cathode ray tube 46.

The clock signal from source 44 is also applied to a reference signal generator 47 which is designed to generate a set of various reference signals such as marker signal, horizontal and vertical blanking signals and gray scale signal. These signals are algebraically combined in an adder 48 with the output signal from the detector 43 and amplified at 49 and applied to the control grid of the cathode ray tube. The clock pulse from the source 44 is also applied to horizontal and vertical deflection circuit 50 to provide a rectangular raster on the cathode ray tube screen.

Details of the piezoelectric transducers are disclosed in the aforesaid U.S. Patent. Each of the ultrasonic transducers comprises a pair of piezoelectric elements each being a rectangular plate of a ceramic composed of $Pb(Mg_{1/3}Nb_{2/3})O_3$, $PbTiO_3$, $PbZrO_3$, with front and back electrode films respectively secured to the front and back surfaces. The piezoelectric plate is polarized in the direction of thickness and has a width-to-thickness ratio equal to or smaller than 0.8 and a considerably large electromechanical coupling coefficient $k_{33}$ or $k'_{33}$ in the direction of its thickness. With either of these coupling coefficients the piezoelectric element has substantially no spurious vibration modes. The electrodes are disposed normal to the direction of the polarization. An impedance matching element is secured to one of the electrodes. The piezoelectric elements as disclosed in the above mentioned U.S. Patent requires very small driving power. This permits the use of integrated circuit complementary metal-oxide semiconductor (CMOS) for the multiplexers 11 and 15 with the result that the control circuit is made compact. This in turn allows part or all of the control circuit to be housed in a casing schematically indicated by a dotted line 11 in FIG. 1 with the transducer unit 10, and consequently allows substantial reduction in the number of connecting wires between the ultrasound probe and display unit, thus facilitating diagnostic operation.

What is claimed is:

1. An ultrasound diagnostic apparatus comprising:
   an array of successively arranged plate-like piezoelectric elements each having a width-to-thickness ratio equal to or smaller than 0.8 and an electromechanical coupling coefficient close to $k_{33}$ or $k'_{33}$ in the direction of the thickness;
   a source of clock pulses;
   a first switching network having a plurality of output terminals connected respectively to said piezoelectric elements to establish access paths between a plurality of input terminals and a group of successively arranged ones of said piezoelectric elements to activate same in response to each of said clock pulses;
   means for causing said first switching network to establish said access paths such that said group of the activated piezoelectric elements is shifted by at least one piezoelectric element in response to each of said clock pulses;
   a second switching network having a plurality of output terminals connected to the input terminals of said first switching network and a plurality of input terminals to establish access paths between said input and output terminals thereof;
   a transmitter having means for generating a train of timing control signals in response to each of said clock pulses and a plurality of amplitude control signals, and a plurality of transmitting channels connected respectively to the input terminals of said second switching network, each of said transmitting channels including an oscillator responsive to a respective one of said timing control signals to generate an ultrasound pulse and an amplitude modulator for modulating the amplitude of said ultrasound pulse in accordance with a respective one of said amplitude control signals;
   means for causing said second switching network to establish said access paths for application of said ultrasound pulses respectively to said activated piezoelectric elements;
   a receiver having means for generating a plurality of phase control signals and a plurality of second amplitude control signals, and a plurality of receiving channels connected to said input terminals of said first switching network to receive signals detected by said activated piezoelectric elements, each of said receiving channels having a phase shifter for imparting a phase shift to the detected signal in accordance with a respective one of said phase control signals and an amplitude modulator for modulating the amplitude of the phase shifted signal in accordance with a respective one of said second amplitude control signals; and
   a display unit responsive to the output signal from said receiver.

2. An ultrasound diagnostic apparatus as claimed in claim 1, wherein each of said piezoelectric element comprises a body of a ceramic material having a tendency to become polarized upon application of an electric field, a pair of plate electrodes secured to the opposite sides of said ceramic body normal to the direction of said polarization, and an impedance matching element secured to one of said electrodes.

3. An ultrasound diagnostic apparatus as claimed in claim 2, wherein said ceramic material is composed of $Pb(Mg_{1/3}Nb_{2/3})O_3$, $PbTiO_3$, $PbZrO_3$.

4. An ultrasound diagnostic apparatus as claimed in claim 1, wherein said first switching network comprises a plurality of analog multiplexers equal in number to the number of said piezoelectric elements of said activated group, each of said multiplexers having an equal number of output terminals, the corresponding output terminals of each said multiplexer being connected respectively to successively arranged ones of said piezoelectric elements.

5. An ultrasound diagnostic apparatus as claimed in claim 4, wherein said second switching network comprises a plurality of analog multiplexers equal in number to the number of said analog multiplexers of said first switching network, each of said multiplexers of the second switching network having an output terminal connected to an input terminal of the corresponding multiplexer of the first switching network and a plurality of input terminals connected together to the input terminals of the other multiplexers of the second switching network.

6. An ultrasound diagnostic apparatus as claimed in claim 1 or 4, wherein said first switching network is housed within a same casing with said array of piezoelectric elements.

7. An ultrasound diagnostic apparatus as claimed in claim 5, wherein said first switching network comprises integrated-circuit complementary metal oxide semiconductor elements.

8. An ultrasound diagnostic apparatus as claimed in claim 1, further comprising means for compensating for exponentially increasing loss of the ultrasonic energy transmitted into a subject human body from said piezoelectric elements.

9. An ultrasound diagnostic apparatus as claimed in claim 8, wherein said compensating means comprises an automatic gain controlled amplifier responsive to the output of said receiver, and means for generating an amplitude modulating signal in response to each of said clock pulses to control the gain of said automatic gain controlled amplifier.

* * * * *